United States Patent [19]

Higgins, III

[11] Patent Number: 6,147,236
[45] Date of Patent: *Nov. 14, 2000

[54] PREPARATION OF STEROL AND STANOL-ESTERS

[75] Inventor: John D. Higgins, III, Ft. Washington, Pa.

[73] Assignee: McNeil-PPC, Inc., Skillman, N.J.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/211,978

[22] Filed: Dec. 15, 1998

Related U.S. Application Data

[63] Continuation-in-part of application No. 09/139,460, Aug. 25, 1998, Pat. No. 5,892,068.

[51] Int. Cl.[7] ...................................................... C07J 9/00
[52] U.S. Cl. ............................................................ 552/554
[58] Field of Search ............................................. 552/554

[56] References Cited

U.S. PATENT DOCUMENTS

| | | | |
|---|---|---|---|
| 1,284,814 | 8/1972 | Erickson . | |
| 4,309,448 | 1/1982 | Takaishi et al. | 424/365 |
| 4,393,044 | 7/1983 | Takada et al. | 424/59 |
| 4,428,885 | 1/1984 | Higaki et al. | 260/410.9 |
| 4,588,717 | 5/1986 | Mitchell | 514/170 |
| 5,270,041 | 12/1993 | Eugster . | |
| 5,502,045 | 3/1996 | Miettinen et al. | 514/182 |
| 5,556,970 | 9/1996 | Kawasaki et al. | 554/190 |
| 5,723,747 | 3/1998 | Lassner et al. | 800/205 |
| 5,892,068 | 4/1999 | Higgins, III | 552/554 |
| 5,958,913 | 2/1999 | Mietene et al. | 514/182 |
| 6,031,118 | 2/2000 | van Amerongen et al. | 552/544 |

FOREIGN PATENT DOCUMENTS

| | | | |
|---|---|---|---|
| 0 127 829 | 2/1988 | European Pat. Off. | C07J 1/00 |
| 0 474 946 A1 | 3/1992 | European Pat. Off. | C11C 3/00 |
| 0 596 135 | 5/1994 | European Pat. Off. | C11C 1/00 |
| 0 190 442 | 11/1998 | European Pat. Off. | C07J 9/00 |
| 0 897 970 A1 | 2/1999 | European Pat. Off. | C11C 3/10 |
| 0 897 971 A1 | 2/1999 | European Pat. Off. | C11C 3/12 |
| 0 911 385 A1 | 4/1999 | European Pat. Off. | C11C 3/00 |
| 1 405 346 | 9/1975 | Germany | C11B 3/00 |
| 19 750 422 | 11/1998 | Germany | C07J 9/00 |
| 44004974 | 8/1965 | Japan . | |
| 51-11113 | 4/1976 | Japan | C07J 9/00 |
| 250583 | 8/1997 | New Zealand . | |
| 1 473 574 | 5/1977 | Spain | C07J 9/00 |
| 1141690 | 1/1969 | United Kingdom | C11C 3/14 |
| 1154230 | 6/1969 | United Kingdom | C11B 3/04 |
| 1284814 | 8/1972 | United Kingdom . | |
| 2148897 | 6/1985 | United Kingdom | C07C 67/08 |
| 2 285 805 | 7/1995 | United Kingdom | C07C 9/00 |
| WO 95/00158 | 1/1995 | WIPO | A61K 37/00 |
| WO 97/24420 | 7/1997 | WIPO | C11C 01/02 |
| WO 97/26804 | 7/1997 | WIPO | A23L 1/30 |
| WO 99/30569 | 6/1999 | WIPO | A23D 7/00 |
| WO 99/39715 | 8/1999 | WIPO | A61K 31/56 |
| WO 99/43218 | 9/1999 | WIPO | A23L 1/30 |
| WO 99/59423 | 11/1999 | WIPO | A23D 9/00 |

OTHER PUBLICATIONS

"Effect of Plant Sterol Esters on the Absorption of Dietary Cholesterol", The Procter & Gamble Company, Mattson, Volpenhein & Erickson, J. Nutr. 107, pp. 1139–1146, (1977).

"Optimizing the Effect of Plant Sterols on Cholesterol Absorption in Man", Mattson, Grundy, & Crouse, The American Journal of Clinical Nutrition 35: Apr. 1982; pp. 697–700.

M. van Dam; D. van Schuppen; American Perfume and Cosmetics, "New Lanolin Acid Esters", vol. 84, No. 8, 1969, pp. 37–40.

*Primary Examiner*—Raymond Henley, III

[57] ABSTRACT

The present invention provides a method for the direct esterification of stanols and sterols with fatty acids to form stanol/sterol-esters. The method provides a synthetic route that is amenable to large scale production of the esters in high yields. A preferred embodiment employs a food grade process free ot organic solvents or mineral acids.

22 Claims, No Drawings

PREPARATION OF STEROL AND STANOL-ESTERS

STATUS OF RELATED APPLICATIONS

This application is a continuation-in-part of U.S. Ser. No. 09/139,460 filed Aug. 25, 1998, now U.S. Pat. No. 5,892,068, the contents of which are hereby incorporated by reference.

FIELD OF THE INVENTION

This invention relates to the preparation of discrete sterol and stanol-esters through a highly efficient acid catalyzed route.

BACKGROUND OF THE INVENTION

It has been shown that the addition of plant sterols, such as. β-sitosterol, to diets will reduce serum cholesterol levels. The sterols reduce serum cholesterol through the disruption of intestinal absorption of dietary cholesterol by displacing it from bile acid micelli. More recently, β-sitosterol's saturated derivative, β-sitostanol, has been shown to be more effective in the reduction of intestinal cholesterol absorption. The sitostanol itself is virtually unabsorbed, so it does not contribute at all to in vivo serum sterol concentration upon consumption. Unfortunately, typical sterols and stanols are insoluble in the micelli phase of the alimentary canal and have only limited solubility in oils and/or fats or water. Hence, free sterols or stanols themselves are not optimum candidates for use in typical pharmaceutical or dietary dosage forms as cholesterol reducing agents.

U.S. Pat. No. 5,502,045 discloses the interesterification of stanols with a fatty acid ester from an edible oil to produce a waxy sterol—ester mixture with improved fat solubility characteristics. Specifically, this patent discloses the reaction of sitostanol interesterified to an edible oil such as rapeseed oil specifically via a base catalyzed transesterification reaction. This is a process that is widely used in the food industry. From a pharmaceutical standpoint, however, interesterification processes such as this have some distinct disadvantages. Primarily, the composition profile of the sterol-ester products are difficult to control since the profile is dependent on the array of fatty acids present in the edible oil employed in the reaction.

In a different approach, German Patent 2035069 discloses the esterification of sterol-esters to fatty acids via a non-food grade process. In particular, thionyl chloride is employed as a reactant which when reacted forms HCl gases as a by-product. Such techniques are not suitable for the production of food grade materials, and they are undesirable in general for large scale reactions.

From a pharmaceutical standpoint, there is an unmet need for a method for the synthesis of discreet stanol/sterol-esters via a bulk food grade process. Discrete compounds are more desirable than mixtures for three main reasons: 1) the composition and performance specifications can be controlled better; 2) structure/activity studies are more feasible; and 3) the physicochemical and chemical properties can be controlled. These advantages of discrete stanol/sterol-esters will be elaborated on later.

SUMMARY OF THE INVENTION

The present invention comprises a method for the direct esterification of stanols or sterols with fatty acids to form discrete stanol/sterol-esters. The method provides a synthetic route that is amenable to large scale production of the stanol-esters in high yield and purity by a food grade process that in a preferred embodiment is free of organic solvents or mineral acids. The method ultimately provides a convenient process that enables one to rationally design discrete stanol/sterol-esters with various physical and biological properties.

DETAILED DESCRIPTION OF THE INVENTION

The present invention provides the direct esterification of stanols and sterols through the reaction of the stanol/sterol and a fatty acid using a food grade acid catalyst. β-sitostanol, the most preferred starting material, is commercially produced from β-sitosterol by a hydrogenation reaction and is commercially available, from various sources including Henkel Corporation.

The fatty acids reacted in the present invention are of the formulae $CH_3-(CH_2)_n-CO_2H$ wherein n is an integer of from 4 to 22. The term fatty acid is well known and understood to those with skill in the art, see for example, *Hawley's Condensed Chemical Dictionary,* Eleventh edition. The term includes acids themselves and salts of these acids. The fatty acids include saturated acids, such as stearic, butyric, lauric, palmitic and the like. Unsaturated fatty acids, including polyunsaturated fatty acids can also be used in the present invention. Suitable fatty acids include oleic, linoleic, linolenic, docosohexanoic acid, conjugated linoleic acid and the like. As disclosed in U.S. Pat. No. 5,554,646, column 1, lines 4448, conjugated linoleic acid is 9,11-octadecadienoic acid, 10,12-octadecadienoic acid, and mixtures thereof. The present invention includes both straight and branched acids, with straight chain acids being preferred.

In the present invention the sterol and stanol-esters have the general formula depicted as Figure I:

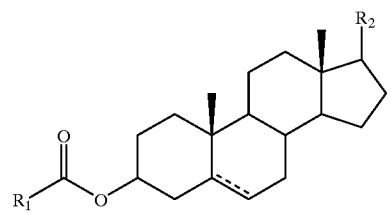

wherein $R_1$ is understood to include aliphatic straight or branched carbon chains ranging from $C_6-C_{23}$, preferably from $C_6-C_{20}$ and most preferably $C_{12}-C_{18}$ groups, and $R_2$ is understood to include aliphatic straight or branched carbon chains ranging $C_3-C_{15}$, preferably $C_6-C_{12}$, and most preferably, $C_9$ groups. More preferably, $R_2$ is selected from the group ($C_1-C_{12}$) alkyl, ($C_1-C_8$) alkoxy, ($C_2-C_8$) alkenyl, ($C_2-C_8$) alkynyl, ($C_3-C_8$) cycloalkyl, halo ($C_2-C_8$) alkenyl, halo ($C_2-C_8$) alkynyl) where halo is understood to include chloro, fluoro, bromo, iodo and the like. Alkyl includes both straight and branched chain groups of carbon atoms. Typical alkyl groups include methyl, ethyl, n-propyl, isopropyl, n-butyl, sec-butyl, isobuytyl, t-butyl, n-pentyl, neopentyl, isopentyl, hexyl, heptyl and the like. The alkyl groups may be halogenated with one, two three or more halogen atoms.

The terms alkenyl and alkynyl included branded and straight chain hydrocarbons having at least one unsaturated bond.

Unsaturation at $C_5$ provides the corresponding sterol-ester. Any stanol or sterol that is functionalized with a hydroxy group is suitable for esterification by the process described herein. Provided below is a generic formula of the stanol/sterols that can be esterified in the present invention

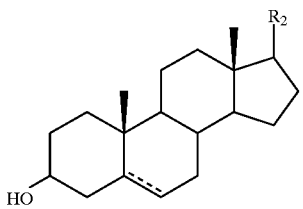

$R_2$ is understood to have the same meaning as set forth above.

Stanols that are capable of being esterified in the present invention include, but are not limited to β-sitostanol.

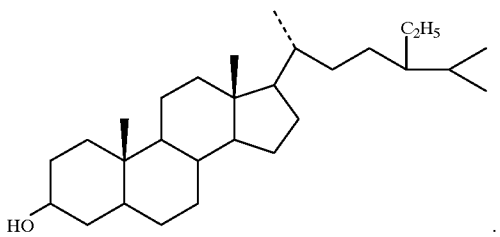

and cholestanol. For example, this process is also amenable to sterols such as β-sitosterol (unsaturated at $C_5$, as shown in Figure I above).

The molar ratios of the starting materials for the esterification reaction, notably the stanol/sterol and the fatty acid, are provided in stoichiometric levels. In a highly preferred embodiment, the fatty acid is present in a 5–10% excess so as to react all of the stanol. Any excess unreacted fatty acid is easily removed in the product workup.

The acid catalyst is typically sufficient if provided at a 1 mole percent as compared to the reactants. The level of catalyst can be increased or decreased to provide the reaction rate desired, however, if too much catalyst is provided a higher than desired level side products may result. Suitable acid catalysts include toluene sulfonic acid, methane sulfonic, sodium hydrogen phosphate, sodium bisulfate and the like. Any acidic proton source can function as the catalyst, although strong mineral acids are not preferred since their use may lead to some decomposition of unsaturated fatty acids during the esterification process. Sodium bisulfate is the preferred catalyst. The catalyst can be in the form of a solid, liquid or gas. Aqueous soluble catalysts are highly preferred since they can easily be removed from the product with water.

One of the most effective aspects of the present invention is that the reaction is performed neat, wherein no solvents are added to the reaction mixture, because the molten fatty acid acts as both a reactant and solvent.

It is particularly appropriate to run the neat reactions under vacuum in order to remove water from the reaction mixture thereby driving the reaction to completion and increasing the yield of the desired ester.

The reaction temperature is conducted at temperatures from about 75 to about 200° C. The preferred range is from about 100 to about 175° C. and most preferably from about 140 to 150° C. The reaction period may vary widely, but for best results and economy the reactions should be allowed to run to completion. Reaction times of greater than 12 hours are common but not necessarily required. One advantage of the present invention is the high yield of the ester product provided by the process. The present process provides yields of greater than 90% and preferably greater than 95%.

The reaction of the present invention is sufficiently mild to prepare esters that were not capable of being synthesized using methods previously disclosed in the art. In particular, the present invention provides a method for preparing esters which are the reaction product of DHA (cis-4,7,10,13,16, 19-docosahexeanoic acid) and CLA (octadecadienoic acid) and the sterol/stanol set forth above. These products are of particular interest in that both DHA and CLA have been reported to possess cholesterol-lowering characteristics. Therefore, a compound which contains the combination of both the stanol or sterol with a pendent ester functionality which when hydrolyzed provides another cholesterol-limiting agent would be highly beneficial. The combination of these functions would be beneficial in that it is reported that the DHA and CLA lower cholesterol in the body by different mechanisms than do sterol and stanol products.

The ester products of CLA and the sterol/stanol are provided below

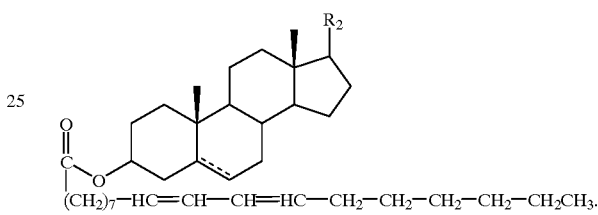

sterol/stanol octadecadienoate; the 9,11-octadecadienoic form is depicted above, and the 10,12 isomer is also common.

More preferably,

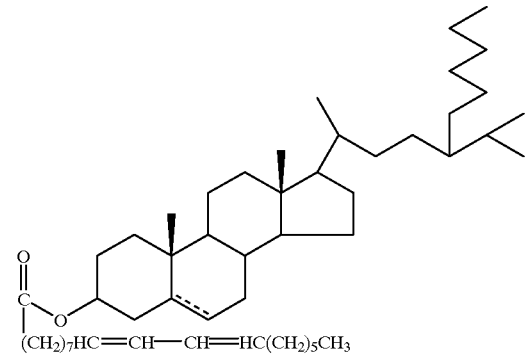

β-sistosterol octadecadienoate

Similarly, the ester product of DHA and sterol/stanol are provided below:

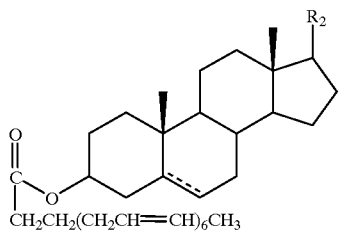

Sterol/stanol docosahexaenoate, and more preferably

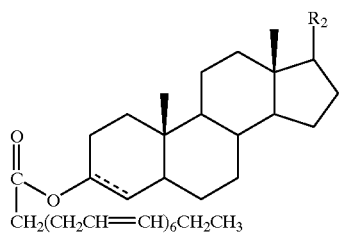

β-sitosterol docosahexaenoate; and
β-sitostanol docosahexaenoate

The present invention also provides a method for reducing serum cholesterol an effective amount of CLA and DHA esters to reduce serum cholesterol. Typically, the level is from about 1 to about 20 g/day, preferably from about 3 to about 15, and most preferably from about 6 to about 9 per day.

Two isolation techniques as described below can be used to isolate the ester reaction product.

Method A: An aqueous/organic solvent extraction isolation may be employed to recover the stanol-ester. Typical organic solvents include dichloromethane, chloroform or toluene. A typical aqueous/organic workup was employed where the ester was extracted into an organic solvent and subsequently isolated after evaporation. For example, the reaction mixture is cooled to room temperature followed by addition of $CH_2Cl_2$. The solution was then washed several times with aqueous $NaHCO_3$. The fatty acid salts are partitioned into the aqueous phase and can easily be removed. The remaining organic phase containing the isolated ester is then dried over anhydrous $NaSO_4$ and decolorized with activated charcoal. When light, non-chlorinated organic solvents (i.e., hexane) are used for extraction, the formation of an inseparable emulsion is observed. Pure esters were recovered as white solids or oils after removal of the solvent on a rotary evaporator and subsequent cooling.

Method B: In a more preferred isolation technique, the ester reaction product is isolated using only water. The crude reaction mixture was diluted with 1% aqueous $NaHCO_3$ and the resulting suspension was stirred rapidly for 1 hour. The pure ester (>95% recovered yield) was filtered and vacuum dried overnight. A calorimetric test for sulfate anion was performed on a small sample of the ester, which showed that no catalyst remained among the product.

Although both methods produced esters identical in purity, the recovered yields (>96%) were better with Method B. This method is also more amenable to large scale synthesis because it gives high purity product without the use of hazardous non-food grade solvents.

The present invention provides several advantages over previous disclosed processes. The present invention provides a method to synthesize substantially discreet stanol-esters rather than mixtures of stanol-esters. As used herein, substantially discreet is understood to mean that the reaction product, the desired ester is provided in a very high proportion of the reaction product. Typically the desired ester is provided in the reaction product in at least 90 percent by weight, more preferably in an amount at least about 98 percent and if the reaction is allowed to run to completion to at least 99 percent by weight. The present invention is capable of providing essentially a single stanol (sterol)-ester, with less than 0.2 weight percent of other ester products. The previously disclosed interesterification processes provide a mixture of the stanol-ester products. For example, the previously disclosed processes provide mixtures of stanol-esters, often with broad ranges of the stanol-esters present (for example, a mixture of 4 esters in ratios of 30, 30, 20, 20 percent by weight). Also in comparison, the previously disclosed direct esterification processes use hazardous, deleterious reagents.

This production of a discreet stanol/sterol-esters has several important advantages over the stanol/sterol-ester mixtures produced by other processes. Firstly, tighter performance specifications (i.e., melting point, specific gravity structural species purity) are possible for discreet compounds. This is because the properties of discreet compounds can be controlled with more precision than for mixtures. Hence, proper performance characteristics and quality of discreet esters are more easily assured as compared to a mixture of ester products.

Furthermore, because the present invention provides the synthesis of discreet stanol/sterol-esters, structure/activity relationships over a range of fatty acid chain lengths can be ascertained. The determination of structure/activity relationships, which are fundamental to rational drug development, are only feasible when screening discreet compounds.

Finally, the gross physical and physiologic properties of the sterol/stanol-ester can be controlled since those properties are dependent upon which fatty acid is employed. For example, esterification to unsaturated fatty acids (i.e., oleic acid) can lead to low melting solids or even liquid products, whereas saturated fatty acid analogs (i.e., stearic acid) tend to lead to higher melting free flowing solids. This ability to so extensively manipulate the physical properties of a high melting sterol is quite unexpected.

The present invention allows the selection of the ester to match the physical properties which are desired. The solid free flowing material is desirable for the manufacture of compressed tablets, or the incorporation of the stanol-ester into baking products. These oil-like stanol/sterol-esters are advantageously employed in the manufacture of soft gel dosage forms or incorporated into a salad dressing or yogurt.

The following examples are provided to further illustrate the claimed invention, but not limit the invention to the examples provided below.

EXAMPLES

The stanol-fatty acid-esters of the invention were prepared by the acid catalyzed esterification reaction method as follows: stanol (10 mmol), fatty acid (12 mmol) and sodium bisulfate (0.12 mmol) were stirred neat under vacuum for 16 hours, at 150° C. The resulting stanol-ester products were isolated using either the technique described above as Method A (employing both water and an organic solvent) or Method B (an aqueous separation process). When glass-like products were formed in method A, they were converted into free flowing solids upon cooling below 0° C. Gas chromatography analysis of crude reaction product indicated that the reactions proceed to greater than 95% completion. Final workup was performed according to methods A or B as described above.

Analytical data for five representative stanol-esters are described below. Analytical data for an ester of cholestanol, as an additional model is also included.

Example 1

β-Sitostanol Stearate was produced by the reaction of β-sitostanol and stearic acid. $NaHSO_4$ was used as the catalyst and the stigmastanol stearate was isolated using Method A described above.

The analytical results for the isolated stigmastanol stearate was as follows:

$^1$HNMR (CDCl$_3$):(4.60(quintet, 1H), 2.19(t, 8, 2H), 1.88 (d, 12, 1H); IR (cm$^{-1}$, KBr): 1739(s, C=O), 1454(m), 1388(m), 1182(s, C—O), 725(m); Elemental Analysis for C$_{47}$H$_{86}$O$_2$: calculated: C, 82.55%; H, 12.59%; found: C, 82.70%; H, 12.50%; Melting Point (DSC): 103–105° C.

Example 2

β-Sitostanol Stearate was produced by the reaction of β-sitostanol and stearic acid. NaHSO$_4$ was the catalyst used and the stigmastanol stearate was isolated using Method B as described above.

The analytical results of the isolated compound is presented below:

$^1$HNMR (CDCl$_3$): (4.62, quintet, 1H), 2.18(t, 8, 2H), 1.88(d, 12, 1H); IR (cm$^{-1}$, KBr): 1739(s, C=O), 1467(m), 1381(m), 1176(s, C—O), 718(m); Elemental Analysis for C$_{47}$H$_{86}$O$_2$: calculated: C, 82.55%; H, 12.59%; found: C, 82.31%; H, 12.63%; MP (DSC): 101–104° C.; % H$_2$O (Karl Fischer) 0.73%

Example 3

β-Sitostanol Palmitate was produced by the reaction of β-sitostanol and palmitic acid. NaHSO$_4$ was employed as a catalyst and the stigmastanol palmitate was isolated using the procedure described above as Method A. The analytical results of the isolated stigmastanol palmitate is presented below:

$^1$HNMR (CDCl$_3$): (4.68(quintet, 1H), 2.24(t, 8, 2H), 1.95(d, 12, 1H); IR (cm$^{-1}$, KBr): 1739(s, C=O), 1460(m), 1394(m), 1176(s, C—O), 725(m); Elemental Analysis for C$_{45}$H$_{82}$O$_2$: calculated: C, 82.57%; H, 12.54%; found: C, 82.59%; H, 12.53%; Melting Point (DSC): 102–104° C.

Example 4

β-Sitostanol Oleate was produced by the reaction of β-sitostanol and oleic acid. NaHSO$_4$ was employed as a catalyst and the stigmastanol oleate was isolated using the technique described as Method B. The analytical results are presented below:

$^1$HNMR (CDCl$_3$): (5.27(m, 2H), 4.62(quintet, 1H), 2.23 (t, 8, 2H); IR (cm$^{-1}$, neat): 1739(s, C=O), 1461(m), 1387 (m), 1176(s, C—O), 1010(m), 718(m); Elemental Analysis for C$_{47}$H$_{84}$O$_2$: calculated: C, 82.80%; H, 12.33%; found: C, 82.98%; H, 12.36%; Melting Point (DSC): 41–44° C.

Example 5

Cholestanol Oleate was produced by the reaction of cholestanol and oleic acid. NaHSO$_4$ was used as a catalyst and the cholestanol oleate was isolated using the technique described as Method A. The analytical results are presented below:

$^1$HNMR (CDCl$_3$): (5.30(m, 2H), 4.65(quintet, 1H), 2.22 (t, 8, 2H); IR (cm$^{-1}$, neat): 1725(s, C=O), 1454(s), 1367 (m), 1168(m, C—O), 1003(m), 711(m); Elemental Analysis for C$_{45}$H$_{80}$O$_2$: calculated: C, 82.67%; H, 12.25%; found: C, 82.64%; H, 12.34%; Melting Point (DSC): 20–25° C.

Comparative Example

The reaction of canola oil and stanol by an interesterification route provides a product mixture having the following approximate, non-reproducible distribution by weight:

Stanol-oleate 67%
Stanol-linoleate 19%
Stanol-linolenate 9%
Stanol-palmitate 3%.

Example 6

β-Sitostanol docosahexeanoate is produced by the reaction of β-sitostanol and DHA. NaHSO$_4$ was employed as a catalyst and the stigmastanol docosahexeanoate is isolated using the technique described as Method A.

Example 7

β-Sitostanol docosahexeanoate is produced by the reaction of β-sitostanol and DHA. NaHSO$_4$ was employed as a catalyst and the stigmastanol docosahexeanoate is isolated using the technique described as Method B.

Example 8

β-Sitostanol octadecadienoate is produced by the reaction of β-sitostanol and CLA. NaHSO$_4$ was employed as a catalyst and the stigmastanol octadecadienoate is isolated using the technique described as Method A.

Example 9

β-Sitostanol docosahexeanoate is produced by the reaction of β-sitostanol and DHA. NaHSO$_4$ was employed as a catalyst and the stigmastanol docosahexeanoate is isolated using the technique described as Method B.

I claim:

1. A method for producing stanol/sterol-esters comprising providing a stanol/sterol of the formula

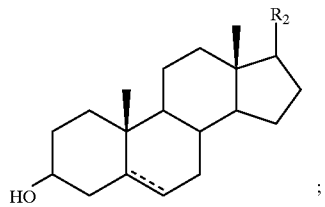

providing an acid, reacting said stanol/sterol and acid in the presence of a mild acid and catalyst resulting in the production of the subtantially discrete corresponding stanol/sterol ester of the formula

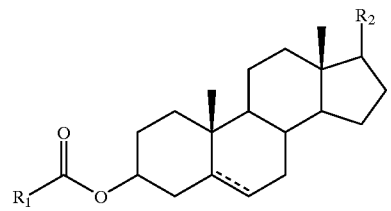

wherein R$_1$ is a carbon chain ranging from C$_6$–C$_{23}$; and R$_2$ is a carbon chain ranging from C$_3$–C$_{15}$.

2. The method of claim 1 wherein the reaction is conducted neat, with the molten fatty acid acting as the solvent.

3. The method of claim 1 wherein the mild acid catalyst is NaHSO$_4$.

4. The method of claim 1 wherein the corresponding sterol/stanol-ester is provided in an amount not less than about 98% by weight.

5. The method of claim 1 wherein $R_1$ of the stanol/sterol-ester has a value of from about from $C_{12}$ to $C_{21}$.

6. The method of claim 1 wherein the reaction temperature is from about 100 to about 200° C.

7. The method of claim 1 wherein the reaction is run under vacuum.

8. The method of claim 1 wherein the isolation of the corresponding stanol/sterol-ester is performed in a completely aqueous process.

9. A method for producing stanol/sterol-esters comprising:

providing a stanol/sterol of the formula

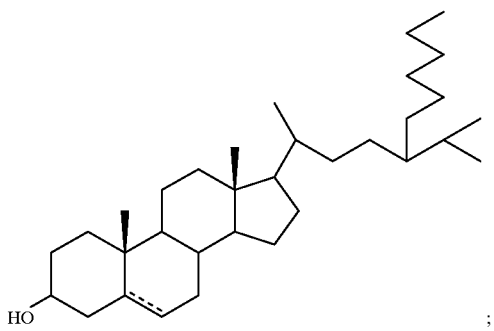

providing a polyunsaturated fatty acid having from $C_6$ to $C_{24}$ carbon atoms in length;

reacting said stanol/sterol and fatty acid in the presence of a mild acidic catalyst, resulting in the production of the substantially discrete corresponding stanol/sterol-ester.

10. The method of claim 9 wherein the reaction is conducted neat, with the molten fatty acid acting as the solvent.

11. The method of claim 9 wherein the mild acid catalyst is $NaHSO_4$.

12. The method of claim 9 wherein the corresponding stanol/sterol-ester is provided in an amount of not less than about 98% by weight.

13. The method of claim 1 wherein the reaction temperature is from about 100 to about 200° C.

14. The method of claim 9 wherein the reaction is run under vacuum.

15. The method of claim 9 wherein the isolation of the corresponding stanol/sterol-ester is performed in a completely aqueous process.

16. A compound selected from the group consisting of

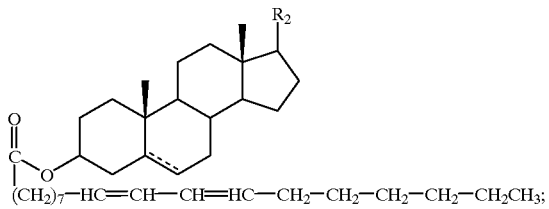

and

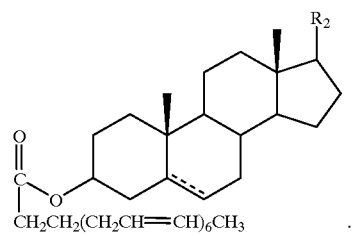

their isomers and mixtures thereof; wherein $R_2$ is a carbon chain ranging from $C_3$–$C_{15}$.

17. The compound of claim 16 wherein $R_2$ is a $C_6$–$C_{12}$ chain.

18. A method for reducing serum cholesterol in a human being by providing an effective amount of the compound of claim 16.

19. The method of claim 18 wherein the effective amount is from about 1 to about 20 mg/day.

20. A compound selected from the group consisting of

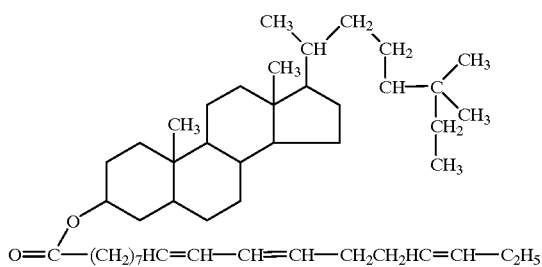

and

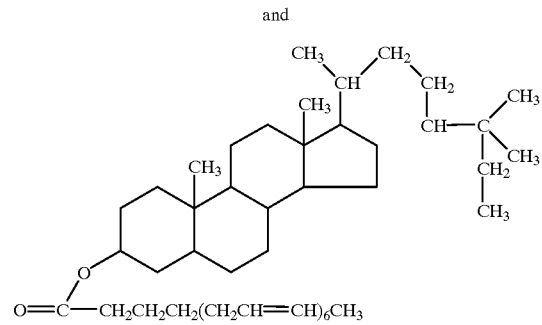

their isomers and mixtures thereof.

21. A method for reducing serum cholesterol in a human being by providing an effective amount of the compound of claim 20.

22. The method of claim 21 wherein the effective amount is from about 1 to about 20 mg/dg.

* * * * *